(12) United States Patent
England et al.

(10) Patent No.: US 10,151,683 B2
(45) Date of Patent: Dec. 11, 2018

(54) CORROSION SENSOR USING ELECTRICAL CONTINUITY

(71) Applicant: Purafil, Inc., Doraville, GA (US)

(72) Inventors: William G. England, Suwanee, GA (US); Matthew Potts, Atlanta, GA (US)

(73) Assignee: PURAFIL INC., Doraville, GA (US)

( * ) Notice: Subject to any disclaimer, the term of this patent is extended or adjusted under 35 U.S.C. 154(b) by 193 days.

(21) Appl. No.: 14/757,384

(22) Filed: Dec. 23, 2015

(65) Prior Publication Data
US 2016/0178549 A1 Jun. 23, 2016

Related U.S. Application Data

(60) Provisional application No. 62/095,872, filed on Dec. 23, 2014.

(51) Int. Cl.
*G01N 17/04* (2006.01)
(52) U.S. Cl.
CPC .................... *G01N 17/04* (2013.01)
(58) Field of Classification Search
CPC ... G01V 3/18; G01V 1/52; G01V 3/34; G01V 3/38; G01V 5/04
USPC .......................... 324/346, 333, 334, 338, 339
See application file for complete search history.

(56) References Cited

U.S. PATENT DOCUMENTS

| 3,605,920 | A | * | 9/1971 | Woodward | E21B 25/00 175/239 |
|---|---|---|---|---|---|
| 2010/0224913 | A1 | * | 9/2010 | Chiang | G01N 17/04 257/253 |
| 2011/0175633 | A1 | * | 7/2011 | Dobashi | G01M 5/0025 324/700 |
| 2016/0091413 | A1 | * | 3/2016 | Kim | G01N 17/02 204/404 |

* cited by examiner

*Primary Examiner* — Giovanni Astacio-Oquendo
(74) *Attorney, Agent, or Firm* — Kilpatrick Townsend & Stockton LLP

(57) ABSTRACT

A method and apparatus for monitoring and reporting corrosion in terms recognized as conforming to an industry standard includes coating a substrate with a corrodible metallic substance of predetermined thickness, passing a current through the metallic substance, and generating a signal when electrical continuity is broken due to corrosion of the metallic substance. In one embodiment the apparatus includes a printed circuit board onto which the coated substrate is mounted, a power source for applying an electrical current across the coated substrate, and a display (such as a light or LCD panel) for providing an indication/alert that electrical continuity has been broken due to corrosion of the metallic substance. A corrosion sensor according to the present invention finds application in such environments as industrial process measurement and control rooms, motor control centers, electrical rooms, semiconductor clean rooms, electronic fabrication sites, commercial data centers, museums, libraries, and archival storage rooms.

15 Claims, 1 Drawing Sheet

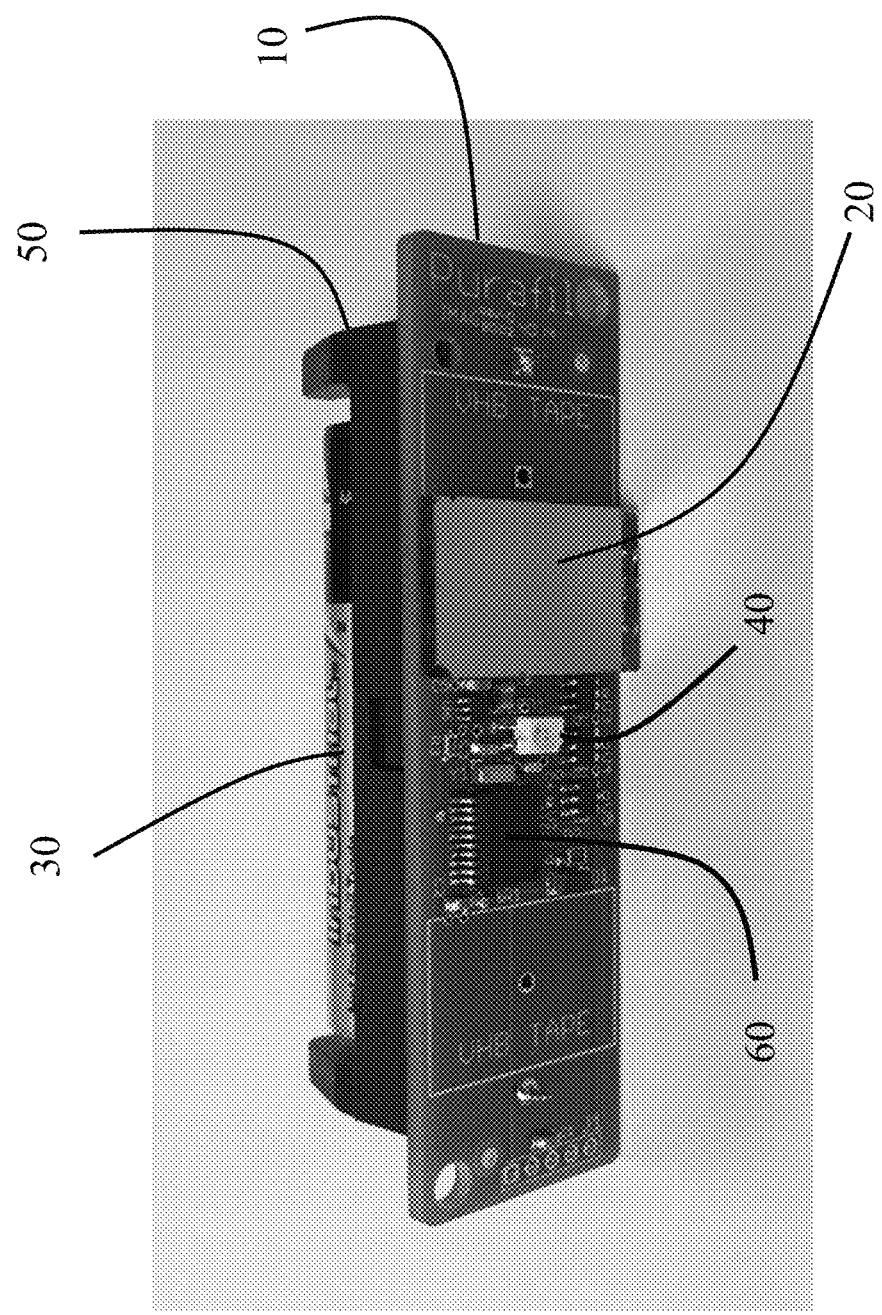

CORROSION SENSOR USING ELECTRICAL CONTINUITY

FIELD OF THE INVENTION

This invention relates generally to a method and apparatus for monitoring corrosion and particularly to a method of identifying corrosive environments in terms of an industry accepted standard of corrosion thickness.

BACKGROUND

Many metal-containing devices and structures must function in corrosive atmospheres which cause them to deteriorate over time. Corrosion may take the form of metal oxides resulting from reaction with oxygen in the air, or by compounds formed with the effluent of industrial processes, such as hydrogen sulfide.

In the electronics industry, for example, approximately one-third of all warranty repair work is attributable to corrosion. Accordingly, the ability to accurately monitor corrosion and take appropriate measures to deter its spread are of utmost importance to the industry.

The standard method of monitoring corrosion has historically been accomplished using a reactivity monitoring procedure such as the so-called "coupon" method. In this method, strips of copper are placed in the environment where corrosion is to be monitored. The coupons carry an initial copper oxide corrosion thickness of about 100 Angstroms (Å). After a period of time in the environment, usually around thirty to ninety days, the coupon is collected and the change in thickness of corrosive buildup on the strips, or coupons, is measured using a complex coulometric reduction procedure, well known to those skilled in the art.

Using an accepted standard such as Standard No. ISA 71.04-2013 set by the International Society of Automation ("ISA") of Research Triangle Park, N.C. (attached hereto and incorporated in its entirety by this reference), this change in thickness is then projected over a chosen period of time. This standard has been endorsed by several trade groups/organizations, including the International Electronics Manufacturing Initiative ("iNEMI") (see attached, incorporated in its entirety by this reference). Other organizations, such as Battelle of Columbus, Ohio, have also developed such standards which, like the ISA standard, are based on reactivity monitoring techniques. Given a corrosive buildup after any number of days, the standard may be applied to project the weekly, monthly, or annual buildup of corrosion in the environment. Such information is vital to the electronics industry in determining the reliability and projected lifetime of equipment. It may affect the scope or duration of warranty coverage, particularly in limiting such coverage when the equipment will be used in corrosive environments. The reactivity monitoring method of corrosion monitoring using coupons is discussed in further detail in "Environmental Conditions and Process Measurement and Control Systems: Airborne Contaminants," a 1985 ISA publication; and Krumbein, Newell, and Pascucci, "Monitoring Environmental Tests by Coulometric Reduction of Metallic Control Samples," *Journal of Testing and Evaluation*, Vol. 17, No. 6, November 1989, pp. 357-67, both of which are incorporated herein in their entirety by this reference.

One major disadvantage of the coupon method of corrosion monitoring is the time frame needed to place the coupon and then analyze the coupon. The coupon method is a passive corrosion monitoring system that cannot provide instantaneous feedback when a certain corrosion threshold is reached.

Real-time corrosion monitoring has been achieved by using quartz crystal microbalance ("QCM") based sensor systems that measure the change in frequency of a quartz crystal resonator caused by the loss or addition of a mass due to corrosion of the sensor. While QCM-based corrosion monitoring systems can provide real-time information regarding corrosion in an environment, such systems are complicated and expensive.

SUMMARY

The terms "invention," "the invention," "this invention" and "the present invention" used in this patent are intended to refer broadly to all of the subject matter of this patent and the patent claims below. Statements containing these terms should not be understood to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to the entire specification of this patent, all drawings and each claim.

Broadly described, the present invention provides methods and systems for using a corrodible metallic substance of pre-determined thickness to monitor and indicate corrosion in terms recognized as conforming to an industry standard. The present invention also relates to methods for calculating the initial thickness of the corrodible metallic substance.

In one embodiment, the present invention provides a method of and system for monitoring corrosion in a corrosive atmosphere, the method including using a corrodible metallic substance as an electrical continuity corrosion sensor and generating a signal when the circuit is broken by advanced corrosion. More specifically, the method may include coating a substrate with a corrodible metallic substance of predetermined thickness or providing a substrate with a corrodible metallic substance of predetermined thickness, passing a current through the metallic substance, and generating a signal when electrical continuity is broken due to corrosion of the metallic substance.

In certain embodiments, the invention includes a light or other electronic display that turns color when the circuit is broken. More specifically, the apparatus includes a printed circuit board onto which the coated substrate is mounted, a power source for applying an electrical current across the coated substrate, and a display (such as a light or LCD panel) for providing an indication/alert that electrical continuity has been broken due to corrosion of the metallic substance. This "open and closed" circuit signal represents the susceptibility of the environment to corrosive attacks based on ISA and other reporting standards. These standards set forth the suggestions that corrosion be kept under a certain number of Angstroms, depending on the type of corrodible metallic substance, to mitigate possible electronic failures.

In some embodiments the thickness of the corrodible metallic substance to be applied to the substrate is calculated by identifying the most likely contaminant/corrosion product in the environment, determining the physical properties of the metallic substance to be used in the system (including the corrosion rate of the metallic substance in the presence of the contaminant), identifying the acceptable (e.g., according to a standard) amount of corrosion on the metallic substance in the presence of the contaminant over a certain time period (e.g., 6 months), and calculating the initial thickness for the metallic substance based on these factors.

A corrosion sensor according to the present invention finds application in such environments as industrial process measurement and control rooms, motor control centers, electrical rooms, semiconductor clean rooms, electronic fabrication sites, commercial data centers, museums, libraries, and archival storage rooms.

BRIEF DESCRIPTION OF THE DRAWINGS

Illustrative embodiments of the present invention are described in detail below with reference to the following drawing FIGURES:

FIG. 1 is an exemplary corrosion sensor according to an embodiment of the invention.

DETAILED DESCRIPTION

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

As discussed herein, continuity refers to being part of a complete or connected whole. In electrical applications, when an electrical circuit is capable of conducting current, it demonstrates electrical continuity. It is also said to be "closed," because the circuit is complete. If enough corrosion occurs then the electrical circuit is not capable of conducting current and is said to be "open", because the circuit is not complete.

Generally, embodiments of the invention relate to methods and systems for using a corrodible metallic substance of pre-determined thickness to monitor and indicate corrosion in terms recognized as conforming to an industry standard. The corrodible metallic substance is included in an electrical circuit. The initial thickness of the corrodible metallic substance can be based upon how much corrosion product will occur in a given time-frame to comply with industry standards.

The calculation of the amount of resultant corrosion product by measuring a mass gain on a metallic surface has been described in William H. J. Vernon, "The Formation of Protective Oxide Films on Copper and Brass by Exposure to Air at Various Temperatures," *Journal of the Chemical Society* (1926, pages 2273-2282). The calculation by William H. J. Vernon is comparable to the use of coulometric reduction with the so-called "coupon" method, as evidenced by Campbell and Thomas, "TARNISH STUDIES: The Electrolytic Reduction Method for the Analysis of Films on Metal Surfaces," *Journal of the Electrochemical Society* (1939, pages 303-328). Each of these studies document the validity of calculating corrosion product estimates by weight gain and weight gain measurement's agreement with coulometric reduction techniques for corrosion product estimates in Angstroms.

In the present invention, a desired corrosion product film thickness is converted to an original amount of metal needed to completely convert that metal to a corrosion product. It has been found that controlling the thickness of the corrodible substance enables one to control the amount of corrosion product capable of being produced and thus provide a determination of air quality based solely on time of exposure. In contrast to the reactivity monitoring "coupon" method that requires analysis after a period of time in the environment, the electrical continuity corrosion sensor acts as an approval or warning in the environment, real-time.

One disadvantage of the reactivity monitoring coupon method is that such coupons, when prepared according to the ISA standard, do not take into account the initial thickness of the corrodible substance before exposure and during analysis, insofar as a significant amount is used to allow for coulometric reduction as method for analysis. In contrast, the methods and systems of the present invention allow for a determination of the amount of corrodible substance that must be used to produce a specific amount of corrosive product to break the circuit that has been provided. Embodiments of the invention thus relate to a method for determining the exact amount and thickness of a metallic corrodible substance required to produce a determined amount of corrosion product that agrees with coulometric and mass gain evaluation methods.

Methods and systems for monitoring and reporting corrosion in terms recognized as conforming to an industry standard thus include coating a substrate with a corrodible metallic substance of predetermined thickness or providing a substrate with a corrodible metallic substance of predetermined thickness, passing a current through the metallic substance, and generating a signal when electrical continuity is broken due to corrosion of the metallic substance.

With specific reference to FIG. 1, the system includes a printed circuit board (10) onto which a coated substrate (20) is mounted, a power source (30) for applying an electrical current across the coated substrate, and a display (40), such as a light, LED or LCD panel, for providing an indication or alert that electrical continuity has been broken due to corrosion of the metallic substance.

The coated substrate includes a substrate material and a corrodible metallic substance applied to the substrate material. The corrodible metallic substance may be applied as a coating to the substrate material by any method capable of controlling the initial thickness of the corrodible metallic substance. One such method includes physical vapor deposition ("PVD"). Other methods may include, but are not limited to, film and rolling application. One company capable of applying a metallic coating having a precise thickness onto a substrate (e.g., a glass slide) is EMF Corporation, in Ithaca, N.Y. (see http://coatings.emf-corp.com/category/test-slides).

The substrate material may be any material capable of bonding to the corrodible metallic substance or to a binding layer applied between the substrate material and the corrodible metallic substance. Suitable substrate materials include, but are not limited to, glass, semiconductor, plastic, printed circuit boards, fiberoptics, metal substrates or other electronic components. Suitable corrodible metallic substance include any corrodible metal, and also include such metals coated with gold. Examples of suitable corrodible metallic substances, without limitation thereto, include copper, silver, nickel, cobalt, permalloy, aluminum, gold, zinc, platinum, molybdenum, titanium, tungsten, combinations/alloys of these metals, and laminates of such metals which may or may not be coated with gold.

A binding layer may be provided between the substrate material and the corrodible metallic substance to improve the adhesion of the corrodible metallic substance to the substrate material. One exemplary suitable binding layer includes, but is not limited to, yttrium oxide ($Y_2O_3$). In contrast to most traditional binding materials which are conductive, the material used in the binding layer of embodiments of the invention should be non-conductive so that the binding layer would not provide an electric current across the coated substrate, which would prevent the circuit from being broken when the corrodible metallic substance has corroded.

As shown in FIG. 1, the power source (20) may be a battery attached to the system/printed circuit board (10) by way of a battery housing (50). In other embodiments (not shown), a power cable could provide power to the printed circuit board rather than a battery. A battery may be desirable in some embodiments to allow for more portability of the apparatus. If used, a battery should preferably have a battery life at least as long as the amount of time the corrodible metallic substance is designed to last (according to the ISA or other standard).

The system may also include a microprocessor or other component for controlling the current applied to the corrodible metallic substance and/or providing a signal to an indicator—including but not limited to a light emitting diode (LED), digital display, audible alarm or other indicator—if the circuit provided between the power source and corrodible metallic substance is broken.

The system, including the printed circuit board and components mounted thereon (including the battery if used) may be at least partially enclosed in a housing that will protect the system components from physical damage but that will not prevent atmospheric conditions (e.g., corrosive gases or humidity) from affecting the corrodible metallic substance.

Embodiments of the invention may further be described with reference to the following non-limiting examples.

EXAMPLE THEORETICAL CALCULATION

Prior Art Coupon Method:

In the coupon method, a corrosion coupon is assembled with a strip of corrosive metal and then analyzed once corrosion happens to determine the amount of corrosive material.

Invention:

In the present invention the amount of corrosion is predicted given the amount of corrosive metal available and then set to the ISA standard. For example, the acceptable amount of corrosion for silver in one month is 200 Angstroms. Thus, allowing a silver plated substrate to accumulate 1200 Angstroms of corrosive product would give the system a lifetime of six months. If the circuit breaks within six months due to corrosion, the user will know that the acceptable amount of corrosive gases in the atmosphere has been surpassed. Correctly predicting the amount of corrosion buildup from a specified amount of corrosive metal is neither easy nor obvious.

Using silver as the corrodible metal, the most common corrosion product is silver sulfide. To determine the thickness of silver needed to provide a silver sulfide film having a thickness of 1200 Angstroms, the number of molecules and atoms per Angstrom must be determined for each crystalline structure. To do this, one molar cube of silver sulfide is assumed, and the volume of the cube from the molar mass and density of silver sulfide is calculated. The cube root of the volume of that cube is the length of all sides of the cube.

Next, the number of molecules on one side of the one molar cube of silver sulfide is calculated. Again, assuming one mole of silver sulfide means that the number of silver sulfide molecules in the cube is equal to Avogadro's number ($6.022 \times 10^{23}$). The cube root of Avogadro's number gives the number of molecules along one side of the cube. With this information the number of molecules per unit length can be calculated, which is converted into silver sulfide molecules per Angstrom. By applying this same method to silver the number of silver atoms per Angstrom can be determined. Understanding the chemical reaction silver undergoes with sulfur provides the ratio of silver in silver sulfide to silver. Finally, using the chemical reaction ratio for silver, silver sulfide molecules per Angstrom and silver atoms per Angstrom, an estimate of corrosion product from a given thickness of corrosive metal can be calculated. The present invention thus also relates to methods for determining the initial thickness of a corrodible metallic product for use in the system using the process described above.

The methods and systems according to the present invention can be useful in a variety of applications, including but not limited to environments such as industrial process measurement and control rooms, motor control centers, electrical rooms, semiconductor clean rooms, electronic fabrication sites, commercial data centers, museums, libraries, and archival storage rooms. Further, they can be used in reliability and warranty applications. The system is small and portable and thus easily located in various environments and locations. Further, unlike previously known real-time monitoring systems, which cost thousands of dollars, the system according to the present invention is much less expensive, e.g., a few hundred dollars or even less.

Different arrangements of the components depicted in the drawings or described above, as well as components and steps not shown or described are possible. Similarly, some features and subcombinations are useful and may be employed without reference to other features and subcombinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

We claim:

1. A corrosion sensor comprising
   a. a coated substrate, wherein the coated substrate is coated with a corrodible substance capable of conducting an electric current,
   b. a power source for applying an electrical current across the coated substrate, and
   c. a display for providing an indication that electrical continuity has been broken due to corrosion of the corrodible substance.

2. The corrosion sensor of claim 1 wherein the coated substrate is mounted on a printed circuit board connected to the power source and display, wherein the display provides a detectable signal.

3. The corrosion sensor of claim 2 wherein the signal is a light or electronic display.

4. The corrosion sensor of claim 1 wherein the power source is a battery.

5. The corrosion sensor of claim 1 wherein the substrate is an inert material.

6. The corrosion sensor of claim 1 wherein the corrodible substance is a corrodible metal.

7. The corrosion sensor of claim 1 further comprising a non-conductive binding layer between the substrate and the corrodible substance.

8. The corrosion sensor of claim 7 wherein the binding layer is yttrium oxide.

9. The corrosion sensor of claim 1 further comprising a microprocessor for controlling an amount of electrical current applied across the corrodible substance.

10. A method for monitoring corrosion in an environment comprising
   a. exposing a substrate coated with a corrodible metallic substance to the corrosive environment to allow corrosion,
   b. passing a current continuously through the metallic substance until a signal is detected, wherein the signal is generated when electrical continuity is broken due to corrosion of the metallic substance,
   wherein detection of the signal indicates that the environment contains a corrosive contaminant.

11. The method of claim 10 wherein the environment is selected from the group consisting of an industrial process measurement and control room, motor control center, electrical room, semiconductor clean room, electronic fabrication site, commercial data center, museum, library and archival storage room.

12. The method of claim 10 wherein the signal is a light or electronic display.

13. The method of claim 10 wherein the substrate is coated with a corrodible metallic substance of a pre-determined thickness.

14. The method of claim 13 wherein the pre-determined thickness is calculated by identifying the most likely corrosive contaminant in the environment, determining the physical properties of the metallic substance, identifying an acceptable amount of corrosion on the metallic substance in the presence of the contaminant over an extended period of time, and calculating the initial thickness of the metallic substance.

15. The method of claim 14 wherein the period of time is six months.

* * * * *